United States Patent
Zeltzer et al.

(10) Patent No.: US 10,278,725 B2
(45) Date of Patent: May 7, 2019

(54) LUMBAR PUNCTURE DETECTION DEVICE

(75) Inventors: Paul M. Zeltzer, Encino, CA (US); Lloyd Fischel, Haiku, HI (US)

(73) Assignee: Paul M. Zeltzer, Encino, CA (US)

( * ) Notice: Subject to any disclaimer, the term of this patent is extended or adjusted under 35 U.S.C. 154(b) by 2187 days.

(21) Appl. No.: 12/560,140

(22) Filed: Sep. 15, 2009

(65) Prior Publication Data

US 2010/0160865 A1 Jun. 24, 2010

Related U.S. Application Data

(60) Provisional application No. 61/097,085, filed on Sep. 15, 2008.

(51) Int. Cl.
 - *A61B 17/00* (2006.01)
 - *A61B 17/34* (2006.01)
 - *A61B 90/00* (2016.01)

(52) U.S. Cl.
CPC ...... *A61B 17/3401* (2013.01); *A61B 2017/00022* (2013.01); *A61B 2090/062* (2016.02); *A61B 2090/0807* (2016.02); *A61B 2090/0811* (2016.02)

(58) Field of Classification Search
CPC ...... A61B 17/3401; A61B 2017/00022; A61B 209/0811; A61B 2090/0807; A61B 2090/062
USPC ........... 600/562–565; 604/117, 272; 606/185
See application file for complete search history.

(56) References Cited

U.S. PATENT DOCUMENTS

| | | | | |
|---|---|---|---|---|
| 3,123,072 A | * | 3/1964 | Bellamy, Jr. | A61M 5/158 285/148.23 |
| 3,693,624 A | * | 9/1972 | Shiley | A61M 16/0465 128/207.15 |
| 3,890,955 A | | 6/1975 | Elliott | |
| 3,893,445 A | * | 7/1975 | Hofsess | A61B 10/025 600/567 |
| 3,964,480 A | | 6/1976 | Froning | |
| 3,993,079 A | * | 11/1976 | Henriques de Gatztanondo | A61B 17/3417 604/164.01 |
| 4,362,156 A | * | 12/1982 | Feller, Jr. | A61M 25/0637 604/165.03 |
| 4,609,370 A | * | 9/1986 | Morrison | A61B 17/3401 600/567 |
| 4,708,147 A | * | 11/1987 | Haaga | A61B 10/0266 600/566 |
| 4,799,495 A | * | 1/1989 | Hawkins | A61B 17/3403 600/567 |

(Continued)

FOREIGN PATENT DOCUMENTS

| | | |
|---|---|---|
| CA | 1306701 | 8/1992 |
| EP | 0139872 | 5/1985 |
| WO | WO2008035333 | 3/2008 |

*Primary Examiner* — Sean P Dougherty

(57) ABSTRACT

A device for drawing spinal fluid from a body part or injecting medication into the body part is disclosed. The device may include one or more measurement features (markings) that indicate the subcutaneous depth of the device as well as confirm placement and orientation of the end of the device in the body part. The device may include a trocar and a cannula having a central passage adapted to receive said trocar. One or more windows may be provided in or on the cannula. Means for venting air from the cannula central passage and/or transparent/translucent material may be disposed in said windows.

19 Claims, 4 Drawing Sheets

(56) References Cited

U.S. PATENT DOCUMENTS

| | | | |
|---|---|---|---|
| 4,838,282 A * | 6/1989 | Strasser | A61B 10/025 600/567 |
| 4,971,068 A | 11/1990 | Sahi | |
| 5,090,408 A * | 2/1992 | Spofford | A61M 16/0472 128/207.14 |
| 5,106,376 A * | 4/1992 | Mononen | A61B 17/3401 604/158 |
| 5,122,121 A * | 6/1992 | Sos | A61M 25/0693 604/256 |
| 5,137,518 A | 8/1992 | Mersch | |
| 5,279,567 A | 1/1994 | Ciaglia et al. | |
| 5,292,309 A | 3/1994 | Van Tassel et al. | |
| 5,297,546 A * | 3/1994 | Spofford | A61M 16/0472 128/207.14 |
| 5,383,859 A | 1/1995 | Sewell, Jr. | |
| 5,447,494 A * | 9/1995 | Dorsey, III | A61M 1/0064 604/118 |
| 5,480,389 A | 1/1996 | McWha et al. | |
| 5,487,392 A * | 1/1996 | Haaga | A61B 10/0275 600/564 |
| 5,569,288 A * | 10/1996 | Yoon | A61B 10/0233 604/165.02 |
| 5,611,778 A | 3/1997 | Brinon | |
| 5,660,186 A * | 8/1997 | Bachir | A61B 10/0233 600/562 |
| 5,810,863 A * | 9/1998 | Wolf | A61B 17/3417 606/167 |
| 5,900,291 A | 5/1999 | Pebbles | |
| 6,159,179 A | 12/2000 | Simonson | |
| 6,200,274 B1 * | 3/2001 | McNeirney | A61B 90/06 128/897 |
| 6,302,852 B1 * | 10/2001 | Fleming, III | A61B 10/025 600/567 |
| 6,312,394 B1 * | 11/2001 | Fleming, III | A61B 10/025 600/567 |
| 6,447,477 B2 | 12/2002 | Burney et al. | |
| 6,592,588 B1 | 7/2003 | Bobic et al. | |
| 6,656,161 B2 | 12/2003 | Young et al. | |
| 6,761,684 B1 * | 7/2004 | Speier | A61B 1/00142 600/121 |
| 6,916,330 B2 | 7/2005 | Simonson | |
| 7,025,746 B2 * | 4/2006 | Tal | A61M 25/0606 604/164.1 |
| 2003/0062644 A1 | 4/2003 | Oyama et al. | |
| 2003/0158521 A1 | 8/2003 | Ameri | |
| 2004/0077973 A1 * | 4/2004 | Groenke | A61B 10/025 600/567 |
| 2004/0092908 A1 | 5/2004 | Harper et al. | |
| 2004/0267154 A1 * | 12/2004 | Sutton | A61B 10/025 600/562 |
| 2005/0159797 A1 | 7/2005 | Chandran et al. | |
| 2007/0016185 A1 * | 1/2007 | Tullis | A61B 18/1477 606/41 |
| 2007/0032794 A1 * | 2/2007 | Weber | A61B 17/1604 606/92 |
| 2007/0066977 A1 * | 3/2007 | Assell | A61B 17/1757 606/96 |
| 2007/0088273 A1 * | 4/2007 | Rafi | A61M 25/0068 604/164.01 |
| 2007/0118050 A1 * | 5/2007 | Accordino | A61B 10/025 600/567 |
| 2007/0255171 A1 * | 11/2007 | Goldenberg | A61B 10/025 600/564 |
| 2008/0045857 A1 * | 2/2008 | Miller | A61B 10/025 600/566 |
| 2008/0097347 A1 * | 4/2008 | Arvanaghi | A61B 10/0233 604/264 |
| 2008/0242930 A1 * | 10/2008 | Hanypsiak | A61B 17/3421 600/114 |
| 2008/0275481 A1 * | 11/2008 | Scarpone | A61B 17/3421 606/172 |
| 2009/0012423 A1 * | 1/2009 | Peters | A61B 10/0266 600/567 |
| 2009/0124859 A1 * | 5/2009 | Assell | A61B 17/025 600/184 |
| 2011/0034885 A1 * | 2/2011 | Biyani | A61B 17/8811 604/272 |
| 2011/0054537 A1 * | 3/2011 | Miller | A61B 17/1655 606/279 |
| 2012/0041371 A1 * | 2/2012 | Tal | A61M 25/0606 604/164.08 |

* cited by examiner

LUMBAR PUNCTURE DETECTION DEVICE

CROSS-REFERENCE TO RELATED APPLICATIONS

The present invention and application relates to, and claims the benefit of the earlier filing date and priority of U.S. Provisional Patent Application No. 61/097,085 filed Sep. 15, 2008, for Lumbar Puncture Detection Device.

FIELD OF THE INVENTION

The present invention relates to apparatus for detecting the accurate insertion of a lumbar puncture needle into a body part containing spinal fluid.

BACKGROUND OF THE INVENTION

The spinal canal contains fluid that bathes, feeds and protects the outer and innermost reaches of the nervous system. A spinal tap is a procedure which takes samples of a patient's cerebrospinal fluid (commonly called CSF). Spinal taps are performed when the physician suspects that the patient may have bleeding (such as subarachnoid hemorrhage, stroke) or an infection of the central nervous system (such as meningitis or encephalitis) or cancer within the nervous system. These procedures are often performed in the emergency room but can be performed in a doctor's office or in a hospital setting.

Before beginning a spinal tap procedure, the physician, or another medical professional, arranges the contents of a spinal tap "kit" on a tray next to where the physician will be sitting. The "kit" may consist of four sterile tubes, a spinal needle (with a stylet (also referred to as a trocar in the instant application) inserted through the spinal needle (also referred to as a cannula in the instant application), along with items for sterilizing the patient's skin and draping the patient.

For the procedure, the patient is asked to lie down in a curled-up position, exposing the back. The physician then sterilizes the patient's back and numbs the skin around the insertion point—a "sterile prep and drape." The physician then inserts a spinal needle, with a stylet inside the spinal needle, between the patient's lumbar (L) vertebrae (usually between the third and fourth (L3-4) or fourth and fifth (L4-5) vertebrae) and blindly advances the needle, with the stylet's beveled and pointed end extending from the end of the needle, through key ligaments until the needle has reached the fluid-filled area surrounding the patient's spine, the subdural/subarachnoid space. The stylet is used to prevent the tip of the spinal needle from becoming blocked by tissue as the needle passes through skin and other tissues or advancing skin cells into the spinal canal where a tumor may form. The stylet's beveled and pointed end may also assist penetration into the spinal ligaments by virtue of being pointed and sharp.

Once the needle is in place, and possibly rotated, the stylet is withdrawn from the spinal needle (cannula) and placed on the sterile tray. The operator must then wait (seconds to minutes) for the CSF to flow through the needle and drip from the proximal end of the needle. The physician looks at the fluid to make a visual determination if it is water-like 'clear' or 'blood-tinged' or another color. He then takes four sterile tubes in sequence from the tray and fills the tubes each with approximately 1 ml (1 cc) of CSF. Once collected, CSF is then sent to a laboratory to determine if the patient is suffering from viral, bacterial or fungal infection of the brain or supporting structures, or cancer among other possible diagnoses. The CSF may also be examined for white and red blood cells and chemical components.

Lumbar puncture needles may have two purposes after entry into the subarachnoid space: withdrawal of spinal fluid and/or injection of antibiotics, chemotherapy or other drugs (but not anesthetics). While some prior patents refer to specific epidural needles as 'spinal needles' (see for example U.S. Pat. No. 5,848,996), such needles are not "spinal tap" needles.

The lumbar puncture procedure can be risky and very uncomfortable for the patient, especially so if the patient is very young or very sick, which is often the case. Very young patients are more likely to move at any time while the physician removes the stylet, waits to view the quality of CSF, reaches for a test tube, places the test tube in the proper position to collect CSF, fills the tube, screws the cap back on and reaches for the next tube, all while CSF is flowing from the patient. The significant risks include: lacerating a spinal nerve (causing pain, then numbness), lacerating the meninges (causing permanent or persistent leaks of CSF), or bleeding (complicating the interpretation of laboratory results). Patients also can develop severe side effects from the loss of too much CSF, including severe headaches. In addition, there is the risk of respiratory arrest in newborns who are held in a curled-up position for the duration of the procedure. Reducing the procedure duration would mitigate these risks.

The lumbar puncture procedures are often performed in emergency rooms where physician time is at a premium. Minutes shaved from a procedure, performed several times over the course of a shift, may result in the physician being able to tend to additional patients. Enhancing the chances of stopping the needle cannula at the correct depth and therefore not causing a hemorrhage by overshooting and puncturing a blood vessel also would reduce the patient's discomfort and risk. Increasing accuracy and precision will reduce procedure time and possible complications mentioned above.

FIG. 2 illustrates a typical spinal tap/lumbar puncture procedure where a lumbar puncture needle 108 is inserted at levels L3-4 or L4-5 of the spine 110 to remove spinal fluid from subarachnoid space 112 (spinal canal diameter=¼-½ inch). The spinal cord 114 and epidural space 116 are also shown. The dural membrane separates the subarachnoid space 112 from the epidural space 116. Typically, a spinal tap needle has a solid stylet or trocar (see e.g., element 40 in FIGS. 4 and 5) with a sharp bevel-pointed end that is disposed flush within an elongated hollow cannula prior to introduction of the set into a patient's body. FIGS. 4 and 5 illustrate the shape of the trocar beveled planar surface 42.

The trocar, with the surrounding cannula, then may be inserted a variable distance (1-5 inches) under the skin, passing through firm ligaments as well as a friable membrane that overlay the protected spinal canal (one quarter to one half inch diameter) which lies within and between the vertebrae as shown in FIG. 2. It is preferable for the trocar to be oriented while passing through firm ligaments and the dural membrane such that the planar surface of the trocar is in alignment with (i.e., parallel to) the direction of the longitudinal fibers of the dura and ligaments so that the cutting of such fibers is minimized. Thereafter, the trocar may be withdrawn thereby permitting spinal fluid to flow through the cannula. Alternatively, medication may be injected through the 'lumbar puncture/spinal tap' cannula to disseminate within the spinal fluid spaces to treat cancer or infection, for example. In such cases, the region between vertebrae and depth of the spinal canal from the skin surface, from which the spinal fluid is drawn or medication is to be injected, is not observable by the physician inserting the trocar and cannula set.

A spinal tap, described above, differs from a procedure called an 'epidural', or 'spinal' or 'spinal block'. An epidural needle is an entirely different shape tipped-needle, sometimes having two holes, and is most often inserted just up to the canal on the near side of the dural membrane and then a catheter is threaded up the dural space and anesthetic drugs are injected to provide pain relief. Examples of three known epidural needle tips 100, 102 and 104 are illustrated in FIG. 1. The 'spinal' (epidural) pencil point needles illustrated in FIG. 1 are designed to inject anesthetic through the open ports 101, 103 and 105, respectively. None of epidural-type needles with the open ports 101, 103 and 105 resemble a typical 'spinal tap' needle with a bevel at the end (explained below and shown in FIGS. 4-7).

Epidural needles have one purpose: injection of pain medication in the epidural space. The epidural needle will cause trauma to the dural membrane, with greater chance of post procedure spinal fluid leaks, if it is used to penetrate the dura into the subarachnoid space. An exception to the foregoing that the applicant is aware of is disclosed in U.S. Pat. No. 5,871,470 to McWha which describes a two needle apparatus with an inner needle used specifically to penetrate the subdural space. Despite the one exception noted, it is not common medical practice to use epidural needles to withdraw spinal fluid. If the epidural needle or catheter enters the subarachnoid space, either during insertion or because of catheter migration, the relatively high volumes of epidural anesthetic can cause high spinal anesthesia, increasing the loss of function in the respiratory muscles. In such cases the patient may have trouble breathing, leading to apnea, increasing numbness, or paralysis.

FIG. 3 illustrates a combined spinal/epidural needle 120 with inner lumbar puncture needle 122 of the type disclosed in U.S. Pat. No. 5,871,470 (needle within a needle without a trocar) which is not flush and penetrates into the subarachnoid/subdural space 112 and the epidural space 116 of the spine 110. It is easy for this type of needle (which is rarely used) to occupy both epidural and subdural/subarachnoid spaces, and represents a great danger in injecting anesthetic compounds into both spaces.

The risks associated with an improper insertion of a lumbar puncture needle can be significant and are listed above. Accordingly, improved confirmation of accurate placement of the cannula tip into a spinal fluid containing region is desirable, as well as confirmation of the alignment of the planar surface of the trocar front beveled tip with the longitudinal direction of the fibers of the body that must be pierced by the trocar.

With current technology, confirmation of a successful spinal tap requires the physician to withdraw the inner trocar fully from the cannula and wait seconds to minutes before CSF is observed to flow from the non-patient end of the cannula. If the cannula has not been properly inserted, it may likewise take seconds to minutes for the physician to ascertain this failure by either observing no CSF to flow from the cannula or observing blood or blood-tinged CSF to flow out of the cannula. Further, the cannula may be easily dislodged from proper placement as a result of patient movement or even the act of moving the trocar entirely out of the cannula. Dislodgement of a properly inserted cannula may be particularly problematic (non-diagnostic tap) when conducting a spinal tap on small children or infants.

Due to the afore-noted shortcomings associated with trocar and cannula sets to draw spinal fluid, some physicians have used blood drawing needles to extract CSF, particularly with premature and newborn infants. This misuse has its own hazards due to absence of the trocar and the longer bevel length of the blood drawing needle which can cause tearing of the spinal canal lining, puncture of vertebrae or bleeding from straddling the canal and surrounding tissues without complete connection to the spinal canal.

Furthermore, there is currently no precise way for the operator to know how deep the spinal tap needle has been inserted below the skin. Epidural needle sets for injecting anesthetic compounds into the epidural space have included features for assisting a physician in determining the depth that the cannula tip and/or inserted catheter may precede or be in communication with the spinal fluid-containing regions. Specifically, these sets have included cannulae with rather imprecise depth markings which only permit the physician to approximate the subcutaneous depth of the cannula. An example of such an epidural needle is disclosed in U.S. Pat. No. 5,810,788 to Racz. However, no cannulae designed for diagnostic spinal taps or administration of antibiotic and chemotherapy into the subdural space (i.e., lumbar puncture needles) currently have depth markings of the type disclosed herein.

Accordingly, it is particularly difficult for a physician to accurately determine that the cannula of a lumbar puncture needle is properly inserted for withdrawal of spinal fluid, absent visual inspection of the fluid exiting the non-patient end of the cannula. Differences in the depth of subcutaneous fat, shapes and sizes of vertebral bones, their alignment with other body parts, prevent the operator from knowing the exact depth of the spinal canal that is only 0.25 to 0.5 inches in diameter. The depth variability from the skin surface to spinal canal can measure 1.5 to 5 inches in the adult. It is fairly common for patients who must undergo one spinal tap to have to undergo multiple, follow-up spinal taps. Accordingly, it would be particularly helpful to a physician who has successfully completed a first spinal tap to know the subcutaneous depth the cannula must reach for cannula to enter the hidden spinal canal.

Still further, there is currently no precise way for the operator to confirm the orientation of the beveled patient end of a cannula and/or the beveled planar surface of the trocar relative to the patient's body during needle insertion. Specifically, the applicants are not aware of any cannula needle for lumbar puncture spinal taps that makes it visibly obvious for the operator to know that the face of the bevel point (cannula and trocar) will be correctly aligned to pierce the longitudinal fibers of the protective ligaments, (correct technique) rather than cutting them on a horizontal entry. The latter may be associated with more spinal tap complications such as headache and post-procedure spinal fluid leaks. Accordingly, it would be helpful for a physician to be able to confirm the orientation of the cannula and trocar front tip beveled portions during insertion into the patient's body.

Still further, there is currently no cannula-needle apparatus with an open end bevel tip which includes a window(s) that may allow the operator to view CSF or the color of any fluid drawn with the cannula-needle apparatus earlier without waiting for it to drip from the proximal non-patient end of the cannula (needle). Earlier viewing of CSF by the physician, i.e., earlier than permitted when the physician must first withdraw the trocar and wait for the CSF to drip from the cannula non-patient end, may assist in shortening the length of lumbar puncture procedure time and thus enhance patient safety and comfort. Accordingly, it would be advantageous for a physician to be able to view CSF or other bodily fluids such as blood, prior to complete withdrawal of the trocar.

Still further, there is currently non cannula-needle apparatus with an open end bevel tip which includes window(s) that may allow air that may occupy the space within the cannula between the trocar and the cannula inner wall from venting without letting CSF or other bodily fluids leak through the window(s). Such windows, particularly when combined with window(s) for viewing CSF and other bodily windows, could permit earlier viewing of CSF and non-CSF fluids and provide the advantages of earlier viewing noted above.

SUMMARY OF THE INVENTION

Responsive to the foregoing challenges, Applicant has developed an innovative device for withdrawing spinal fluid from or injecting fluid into a spinal canal, comprising: a trocar having a front tip with a beveled planar surface; a cannula having a beveled patient end, a non-patient end, an outer surface, and a central passage adapted to receive said trocar; a window in the cannula extending from the outer surface to the central passage, said window being spaced a predetermined distance from the cannula beveled patient end; and a transparent or translucent member disposed in said window.

Applicant has further developed an innovative device for withdrawing spinal fluid from or injecting fluid into a spinal canal, comprising: a trocar having a front tip with a beveled planar surface; a cannula having a beveled patient end, a non-patient end, an outer surface, and a central passage adapted to receive said trocar; one or more depth markings on said cannula; and an orientation marking on said cannula.

Applicant has still further developed an innovative device for withdrawing spinal fluid from or injecting fluid into a spinal canal, comprising: a trocar having a front tip with a beveled planar surface; a cannula having a beveled patient end, a non-patient end, an outer surface, and a central passage adapted to receive said trocar; a window in the cannula extending from the outer surface to the central passage, said window being spaced a predetermined distance from the cannula beveled patient end; and a means for venting air from the cannula central passage disposed in said window.

It is to be understood that both the foregoing general description and the following detailed description are exemplary and explanatory only, and are not restrictive of the invention as claimed.

BRIEF DESCRIPTION OF THE DRAWINGS

In order to assist the understanding of this invention, reference will now be made to the appended drawings, in which like reference characters refer to like elements.

DETAILED DESCRIPTION OF EMBODIMENTS OF THE INVENTION

Figure 4:
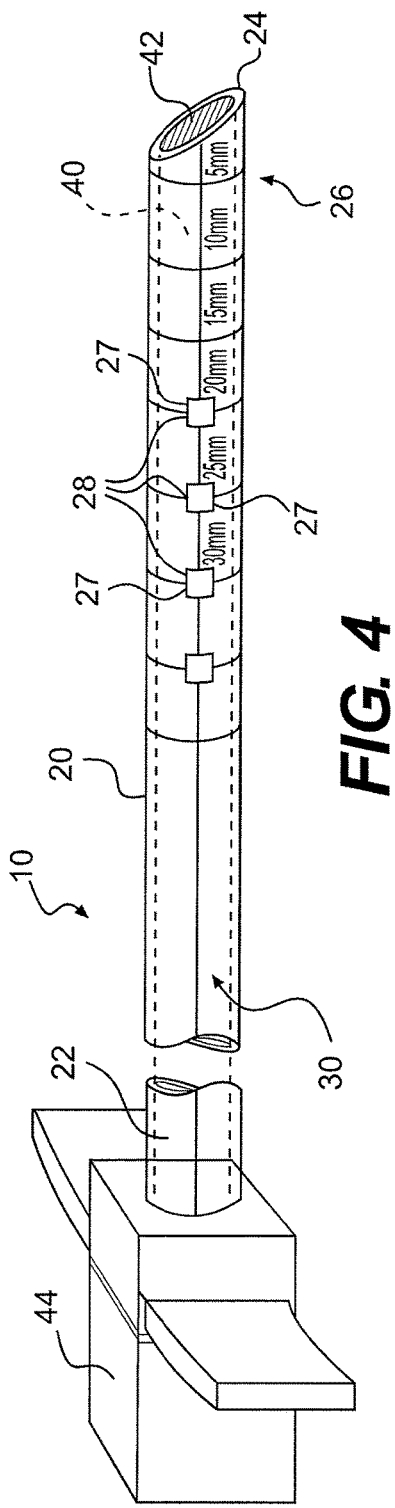
FIG. 4 is a pictorial view a first embodiment of the present invention as configured for insertion of the trocar and cannula set into a vertebrae.

Reference will now be made in detail to a first embodiment of the present invention, an example of which is illustrated in the accompanying drawings. With reference to FIG. 4, a pictorial view of a spinal fluid withdrawing and/or medication injection device 10 is shown. The spinal fluid withdrawing device 10 may include a hollow cannula 20 and a trocar rod (trocar) 40. The cannula 20 may include a cannula non-patient end 22, a cannula patient end 24, one or more depth markings 26, and one or more venting members 28 disposed in windows or openings 27 provided in the cannula wall. The cannula 20 may define a central hollow passage extending longitudinally through the cannula which is adapted to permit spinal fluid to flow through. The windows 27 in the cannula 20 may extend through the cannula wall to the central passage. The windows 27 in which the venting members 28 are disposed may be rectangular, oval or some other shape, preferably may be 1-2 mm wide measured along the axis of the cannula 20, and may preferably be set 10 mm apart, although they are shown to be set 5 mm apart in FIG. 4.

The cannula patient end 24 may be beveled, as shown. The windows 27 in which the venting members 28 are disposed may be set ninety degrees out of alignment with the pointed tip of the bevel of the cannula patient end 24, as well as ninety degrees out of alignment with the planar surface of the trocar 40 front beveled tip, as shown. The ninety degree separation between the windows 27 and the pointed tip of the bevel of the cannula patient end 24 and the planar surface of the trocar 40 front beveled tip may permit a physician to view the windows while inserting the cannula into a patient's body with the cannula in a bevel-sideways position, as is preferred. The windows 27 may be set at such an angle relative to the bevel edge of the cannula 20 and the planar surface of the trocar 40 so that both may be in optimal parallel entry presentation to the ligaments if the windows face upward toward the physician's view. Thus, the windows 27 may permit the physician to confirm that the preferred orientation of the cannula 20 and the trocar 40 is maintained during insertion into the patient's body.

The depth markings 26 may include numeric indications of depth, such as for example, 5 mm, 10 mm, 15 mm, etc., may include etched, engraved or other textured depth indicators, and/or may include different colored bands or any icon to indicate depth. The depth markings 26 are shown to be placed at the same intervals as the windows 27 however it is appreciated that the depth markings need not be placed at the same intervals as the windows and may be between such windows. The cannula 20 may also include etched, engraved or other textured orientation marking 30 which, like the windows 27, may indicate the orientation of the bevel of the cannula patient end 24 and the planar surface of the trocar 40 front beveled tip. The orientation marking 30 may be set at such an angle relative to the bevel edge of the cannula 20 and the planar surface of the trocar 40 so that both may be maintained in optimal parallel entry presentation to the ligaments if the orientation marking faces upward toward the physician's view.

The trocar 40 may include a patient end 42 with a beveled planar surface tip which is adapted to fit flush with the cannula beveled patient end 24, and a non-patient end 44 with a hub to apply insertion or withdrawal pressure to the trocar. The trocar 40 may be sized to fit relatively snugly within the central passage of the cannula 20, while still permitting the trocar to slide within the central passage. Some air space may exist between the central passage of the cannula 20 and the trocar 40 when the trocar is fully inserted. Preferably, the trocar 40 and the cannula 20 may be constructed of rigid material, such as surgical steel or plastic polymers, or the like which are known in the art. The trocar 40 is preferably sufficiently stiff and sharp to permit it to be inserted without damage through a patient's vertebral ligaments and withstand inadvertent insertion into bony vertebrae.

The venting members 28 (i.e., means for venting air) may be disposed in the windows 27 provided in the wall of the cannula 20. The venting members 28 may be sealed in the windows 27 such that fluid within the cannula central passage is prevented from escaping past or around the venting members. In the first embodiment of the present invention, the venting members 28 may be gas, and particularly air, permeable, but at least partially impermeable to a liquid, such as spinal fluid and blood. Preferably, the venting members 28 may be substantially porous for gas constituents less than about 5 microns in size, and substantially non-porous for liquid constituents about 5 microns and greater in size, however, it is appreciated that these approximate sizes should not be limiting for the invention.

The venting members 28 may be constructed of any of a number of materials that provide the desired level of porosity, which may include, but are not limited to sintered, layered, rolled, foamed, perforated, or impregnated, hydrophilic/hydrophobic compositions, porous polyethylene, porous polypropylene, porous polyfluorocarbon, absorbent paper, materials impregnated with dilute Russell Viper venom molded fiber, fiberglass, felt, granular starch, cellulose, polyacrylamide gel, hydrogel, a molded admixture of porous hydrophobic/hydrophilic granules and sufficiently low density silicone, molded open cell polyurethane, and like polymeric materials. Examples of materials that may be used to construct the venting (i.e., porous) members 28 are discussed in U.S. Pat. No. 4,207,870 to Eldridge, and U.S. Pat. No. 4,340,068 to Kaufman, each of which are hereby incorporated by reference. The venting members 28 may further comprise material which is rendered visibly darker or lighter when spinal fluid and/or blood is within the cannula.

Figure 5:
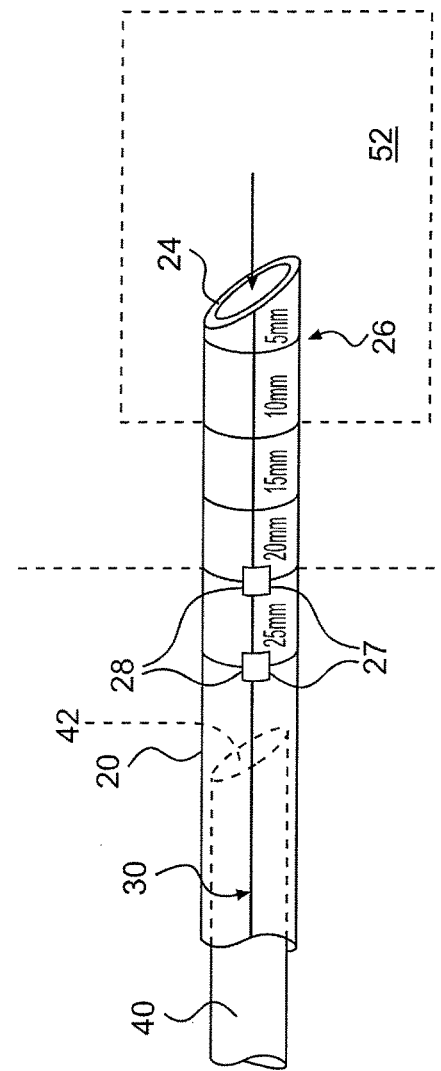
FIG. 5 is a pictorial view of the cannula tip portion of the first embodiment of the present invention after the trocar is partially withdrawn from the cannula tip portion

The function of the first embodiment of the spinal fluid withdrawing device 10 will now be described with reference to FIGS. 4-5. With reference to FIG. 4, the trocar 40 and the cannula 20 may be pushed and/or bored into a patient's inter-vertebral spaces to a depth at which the physician expects the patient end 24 of the cannula may be in communication with the spinal canal and its spinal fluid. Once the cannula 20 is at such depth, the physician may begin to withdraw the trocar 40 out of the cannula 20. If no fluid is detected, the trocar 40 may be re-inserted and the device 10 may be pushed forward or pulled backward, depending upon the physician's belief as to the placement of the cannula 20. With reference to FIG. 5, as the trocar 40 is withdrawn, spinal fluid may flow from the patient 50 spinal canal 52 into the cannula 20 central passage. The spinal fluid may be more readily drawn into the cannula 20 central passage as a result of the venting members 28 permitting air to escape through them. Furthermore, the venting members 28 may be transparent or translucent such that the presence of spinal fluid and/or other bodily fluid such as blood may be visually detected by the physician. Such visual detection may be aided by directly bright light onto the venting members 28. Depending on the material selected for the venting members, it may be rendered visibly shaded (darker) or be clear or colored as is the spinal fluid.

Figure 6:
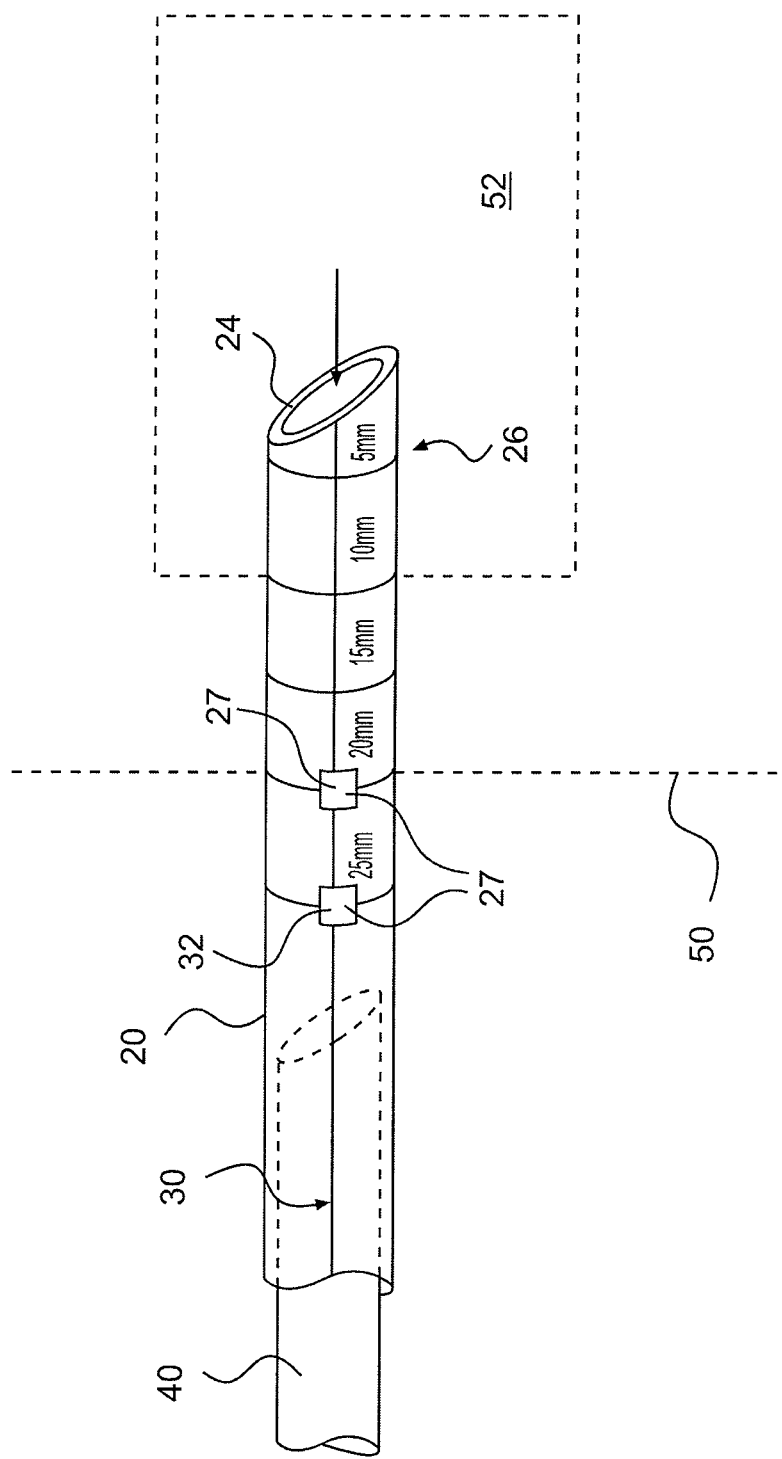
FIG. 6 is a pictorial view of the cannula tip portion of a second embodiment of the present invention after the trocar is fully withdrawn from the cannula tip portion past the windows provided therein.

A second embodiment of the present invention is illustrated in FIG. 6, in which like reference numerals refer to like elements discussed in the previous embodiments of the invention. With reference to FIG. 6, one or more of the windows 27 (and potentially all of the windows) may be provided with a transparent or translucent member 32 which does not act as a venting member. In such an embodiment, it is not necessary for the venting members 28 to be translucent or transparent or to change color in order to visually detect the presence of spinal fluid or other bodily fluids within the cannula 20. The transparent or translucent member 32 may be comprised of plastic or glass material which is suitable for medical applications. The cannula 20 may also be provided with an orientation marking 30 and depth markings 26 in the same manner as in the first embodiment.

Figure 1:
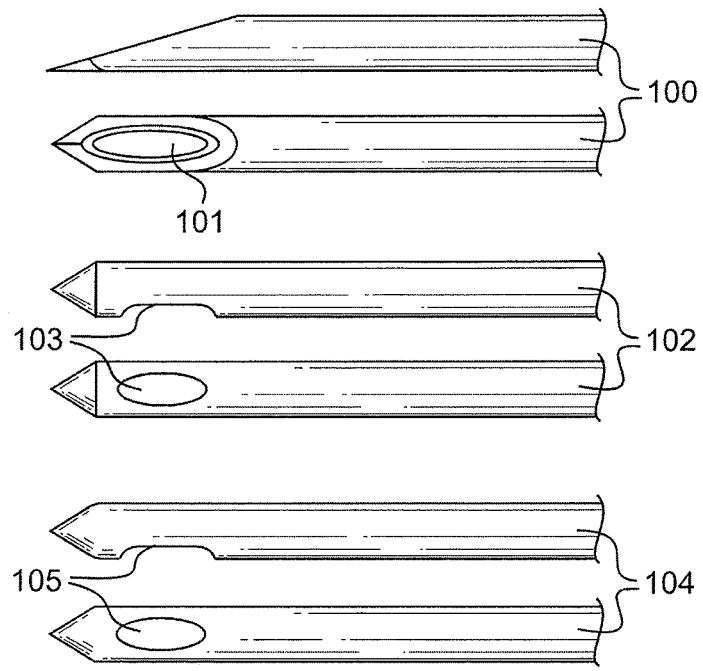
FIG. 1 is a pictorial view of examples of prior art epidural needle tips.
Figure 2:
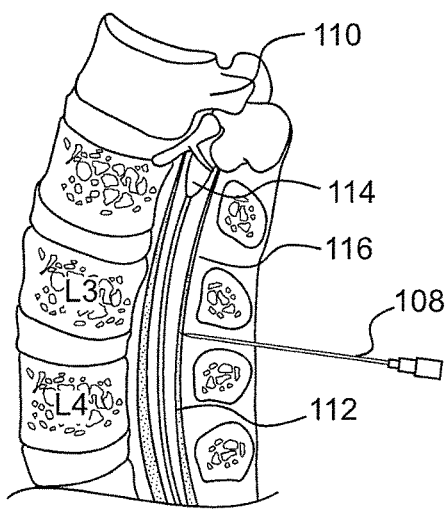
FIG. 2 is a pictorial view of a spine and an inserted lumbar puncture needle.
Figure 3:
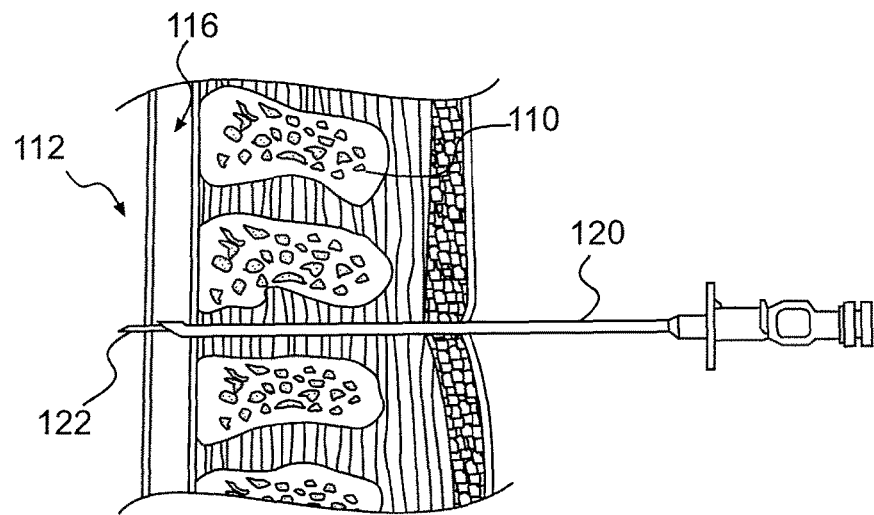
FIG. 3 is a pictorial view of a spine and an inserted combined spinal/epidural needle.
Figure 7:
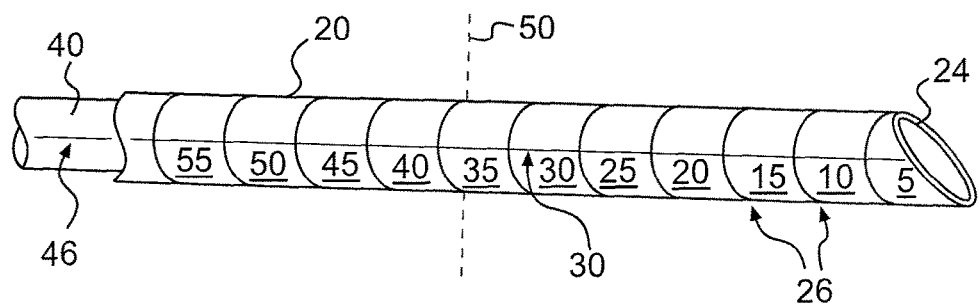
FIG. 7 is a pictorial view of the cannula tip portion of a third embodiment of the present invention after the trocar is withdrawn from the cannula tip portion.

A third embodiment of the present invention is illustrated in FIG. 7, in which like reference numerals refer to like elements discussed in the previous embodiments of the invention. With reference to FIG. 7, the outer surface of the cannula 20 is provided with depth markings (e.g. in millimeters as in FIG. 7) 26 and an orientation marking 30. The trocar rod 40 is provided with an orientation marking 46. The depth markings 26 and orientation markings 30 and 46 may enable the physician to monitor and confirm both the depth and orientation of the bevel of the cannula patient end 24 and the beveled planar surface of the trocar 40 front tip during the lumber puncture procedure.

It will be apparent to those skilled in the art that variations and modifications of the present invention can be made without departing from the scope or spirit of the invention. For example, the shape, size, and material selection for the various components of the spinal fluid withdrawing device may be changed without departing from the intended scope of the invention and appended claims. It is further appreciated that forming one or more elements of the apparatus embodiments of the present invention integrally or separately is intended to fall within the scope of the invention and appended claims.

What is claimed is:

1. A device for withdrawing spinal fluid from or injecting fluid into a spinal canal, comprising:
    a solid trocar rod having a front tip with a beveled planar surface;
    a cannula comprising a shaft having a beveled patient end, a non-patient end, an outer surface, and a central passage adapted to receive said trocar rod;
    a depth marking on said shaft; and
    a first orientation marking on said shaft, wherein said first orientation marking indicates the orientation of the beveled patient end of the cannula;
    wherein the diameter of the shaft at the depth marking and the diameter of the shaft at the first orientation marking are the same.

2. The device of claim 1, wherein said first orientation marking is visible to an operator of the device to confirm a preferred orientation of the beveled patient end, and wherein said preferred orientation of the beveled patient end is provided when the beveled patient end is aligned relative to a patient body so as to minimize severing body fibers during insertion of the device into the patient body.

3. The device of claim 1, wherein the trocar comprises a second orientation marking.

4. The device of claim 3, wherein the second orientation marking is visible to an operator of the device to confirm a preferred orientation of the trocar beveled planar surface, and wherein said preferred orientation of the trocar beveled planar is provided when the trocar beveled planar surface is aligned relative to a patient body so as to minimize severing body fibers during insertion of the device into the patient body.

5. The device of claim 1 wherein the beveled patient end comprises a bevel having a pointed tip; and wherein the first orientation marking is located approximately ninety degrees out of alignment with said pointed tip.

6. The device of claim 5 wherein the depth marking is located approximately ninety degrees out of alignment with said pointed tip, in circumferentially the same direction as the first orientation marking.

7. The device of claim 3 wherein the beveled planar surface of the trocar has a leading edge, and the second orientation marking is located approximately ninety degrees out of alignment with the leading edge.

8. The device of claim 5 wherein the depth marking comprises a number.

9. The device of claim 8 wherein the device further comprises a plurality of depth markings wherein each depth marking comprises a number, and wherein the value of each number increases as the distance between the depth markings and the beveled patient end increases.

10. The device of claim 9 wherein each number indicates a measured distance between the number and the pointed tip of the bevel.

11. A device for withdrawing spinal fluid from or injecting fluid into a spinal canal, comprising:

a cannula comprising a shaft having a beveled patient end, a non-patient end, an outer surface, and a central passage, wherein the beveled patient end comprises a bevel having a pointed tip;
a depth marking on said shaft; and
a first orientation marking on said shaft, wherein said first orientation marking indicates the orientation of the beveled patient end, wherein the first orientation marking is located approximately ninety degrees out of alignment with said pointed tip, and wherein the diameter of the shaft at the depth marking and the diameter of the shaft at the first orientation marking are the same.

12. The device of claim 11 wherein the depth marking is located approximately ninety degrees out of alignment with said pointed tip, in circumferentially the same direction as the first orientation marking.

13. The device of claim 11, wherein said first orientation marking is visible to an operator of the device to confirm a preferred orientation of the beveled patient end, and wherein said preferred orientation of the beveled patient end is provided when the beveled patient end is aligned relative to a patient body so as to minimize severing body fibers during insertion of the device into the patient body.

14. The device of claim 11 wherein the depth marking comprise a number.

15. The device of claim 14 wherein the device further comprises a plurality of depth markings wherein each depth marking comprises a number, and wherein the value of each number increases as the distance between the depth markings and the beveled patient end increases.

16. The device of claim 15 wherein each number indicates a measured distance between the number and the pointed tip of the bevel.

17. The device of claim 12 wherein the depth marking comprises a number.

18. The device of claim 17 wherein the device further comprises a plurality of depth markings wherein each depth marking comprises a number, and wherein the value of each number increases as the distance between the depth markings and the beveled patient end increases.

19. The device of claim 18 wherein each number indicates a measured distance between the number and the pointed tip of the bevel.

* * * * *